(12) United States Patent
Reiner et al.

(10) Patent No.: US 8,039,024 B2
(45) Date of Patent: Oct. 18, 2011

(54) DEVICE AND COMPOSITION FOR THE DELIVERY OF A PRESERVATIVE-FREE BALSAMIC CREAM

(75) Inventors: Alberto Reiner, Como (IT); Giorgio Reiner, Como (IT)

(73) Assignee: APR Applied Pharma Research, S.A., Balerna (CH)

( * ) Notice: Subject to any disclaimer, the term of this patent is extended or adjusted under 35 U.S.C. 154(b) by 219 days.

(21) Appl. No.: 12/358,554

(22) Filed: Jan. 23, 2009

(65) Prior Publication Data

US 2009/0186105 A1 Jul. 23, 2009

Related U.S. Application Data

(60) Provisional application No. 61/022,908, filed on Jan. 23, 2008.

(51) Int. Cl.
*A61K 36/00* (2006.01)
(52) U.S. Cl. .......................................................... 424/725

(58) Field of Classification Search ........................ None
See application file for complete search history.

(56) References Cited

U.S. PATENT DOCUMENTS

| 6,498,197 | B1 * | 12/2002 | Bialek et al. | 516/55 |
| 7,854,940 | B2 * | 12/2010 | Ciccognani et al. | 424/404 |
| 2003/0147825 | A1 * | 8/2003 | Chiarelli et al. | 424/70.11 |
| 2006/0057175 | A1 * | 3/2006 | Ciccognani et al. | 424/405 |
| 2007/0054967 | A1 * | 3/2007 | Schmaus et al. | 514/717 |
| 2008/0206159 | A1 * | 8/2008 | Tamarkin et al. | 424/45 |
| 2008/0306021 | A1 * | 12/2008 | Buerger et al. | 514/54 |

FOREIGN PATENT DOCUMENTS

EP 1634576 A1 * 3/2006

* cited by examiner

*Primary Examiner* — Patricia Leith
(74) *Attorney, Agent, or Firm* — Clark G. Sullivan; Arnall Golden Gregory LLP

(57) ABSTRACT

A device and composition for delivering menthol, camphor, eucalyptus essential oils, and other essential oils with balsamic benefits, to be used for the relief of symptoms of common cold.

7 Claims, 1 Drawing Sheet

DEVICE AND COMPOSITION FOR THE DELIVERY OF A PRESERVATIVE-FREE BALSAMIC CREAM

RELATIONSHIP TO PRIOR APPLICATIONS

This application claims priority to provisional U.S. application 61/022,908, filed Jan. 23, 2008.

FIELD OF THE INVENTION

The present invention relates to a cream with menthol, camphor and eucalyptus essential oils as major components to be used for the relief of symptoms of common cold in adults; and eucalyptus, pine and lavender essential oils for the relief of symptoms of common cold in children. The invention further relates to a device for the delivery of such a cream. Passive inhalation of the components of the cream through the upper respiratory ways improves breathing and relieves nasal congestion caused by the common cold. The cream is filled in a device that allows application of the cream directly to the skin without touching the cream with the hands. The device also allows the aroma from the cream to be inhaled directly from the device.

BACKGROUND OF THE INVENTION

The common cold is a viral infection of the lining of the nose, sinuses, throat, and large airways. Symptoms of the cold start 1 to 3 days after infection. Usually, the first symptom is discomfort in the nose or throat. Later, the person starts sneezing, has a runny nose, and feels mildly ill. Fever is not common, but a mild fever may develop at the beginning of the illness. At first, the secretions from the nose are watery and clear and can be annoyingly plentiful; eventually they become thicker, opaque, yellow-green, and less abundant. Many people also develop a cough. Symptoms usually disappear in 4 to 10 days, although a cough often lasts into the second week.

A person with a cold should stay warm and comfortable and try to avoid spreading the infection to others. Anyone with a fever or severe symptoms should rest at home. Drinking fluids and inhaling steam or mist from a vaporizer may help to keep secretions loose and easier to expel.

Several popular non-prescription remedies that help the symptoms of a cold are available. For example, decongestants help open clogged nasal passages, antihistamines help dry a runny nose, and cough syrups make coughing easier by thinning secretions or suppressing cough. These drugs are most often sold as combinations but can also be obtained individually.

The olfactory region comprises cilia that project downward from the olfactory epithelium into a layer of mucous, which is about 60 microns thick. This mucous layer is a lipid-rich secretion that bathes the surface of the receptors at the epithelium surface. The mucous layer is produced by the Bowman's glands, which reside in the olfactory epithelium.

The mucous lipids assist in transporting the odorant molecules, as only volatile materials that are soluble in the mucous can interact with the olfactory receptors and produce the signals that the human brain interprets as odour.

Each olfactory receptor neuron has 8-20 cilia that are whip-like extensions 30-200 microns in length. The olfactory cilia are the sites where molecular reception with the odorant occurs and sensory transduction (i.e., transmission) starts. The olfactory epithelium also contains another sensory system in the form of "Trigeminal Nerve Receptors". Together with the olfactory receptor system localized in the olfactory bulb, the $5^{th}$ cranial or trigeminal nerve provides a second set of nerve endings which are responsible for tactile, pressure, pain and temperature sensations in the areas of the mouth, eyes and nasal cavity.

A number of chemical trigeminal stimulants produce effects described as hot, cold, tingling or irritating. For example, leavo-menthol produces the trigeminal feeling of "cold" at moderate concentrations and "hot" at high concentrations in the nasal cavity. Similarly camphor, which possesses markedly more aroma than menthol, also produces the "cold" sensation via interaction with trigeminal receptors. [Eccles, 1994; Hensel, 1974; Ohloff, 1994]. Ohloff states, "About 70% of all odours are said to stimulate the trigeminal nerve endings although, in general, they may be several times less sensitive than olfactory receptors". [Ohlofff 1994]

Popular treatments of the common cold include steamy hot bath water that contains small amounts of essential oils, providing warm, moist air to help open nasal and bronchial passages. Essential oils can also be used in many humidifiers or in a tissue scented with the oils.

While steam inhalation is considered to be an effective method of liquefying respiratory tract fluid, a point of dispute is the value of adding volatile aromatic drugs to the water vaporizer, for which there is no evidences of efficacy. [Boyd & Pearson, 1946; Boyd & Sheppard, 1968; Ohloff, 1994]. It can be reasonably argued that the major amount of any drug passively inhaled (by breathing air or vapors) remains in the nose or the oro-pharynx.

Essential oils are traditionally believed to be useful in the symptomatic treatment of nasal congestion and these compounds can be found in several popular remedies in use for many years. Nevertheless the effects of these substances on the nose had been studied very little.

An early study was done in 1927 on the effects of camphor, eucalyptus and menthol sprayed directly onto the nasal mucosa of dogs and humans, which concluded that these substances had no decongestant action but produced only a sensation of nasal patency. The Author suggested that this sensation could be the result of the action on temperature sensitive nerve endings. [Fox, 1927]

Another trial studied the effects of five minutes exposure to camphor, eucalyptus or menthol vapour on nasal resistance to airflow, assessed by rhinomanometry, and nasal sensation in 30 healthy volunteers. None of the essential oils had any significant effect on the nasal resistance (changes in nasal resistance between −10% and +10%), in contrast with 5 min exercise on the cycle ergometer, taken as a control, which produced about 80% reduction in nasal resistance. As far as the subjective impression is concerned, the majority of subjects reported a cold sensation on nasal inspiration. The Authors' conclusion was that "it therefore seems likely that the main property of camphor, eucalyptus and menthol is a stimulant action or sensitising effect on nasal cold receptors and this gives a sensation of increased airflow even though there may be no change in nasal resistance to airflow".

The above results have been confirmed in a subsequent study, where the inspiratory and expiratory nasal resistance to airflow were measured in 35 healthy subjects after inhalation of a mixture of 125 mg menthol+50 mg camphor+10 mg oil of pine+5 mg methyl salicylate, without any effect on the resistance of the left nasal passage.

Eucalyptus was first used by Australian aborigines, who used the leaves as a remedy for fevers. In the 1800s, crew members of an Australian freighter developed high fevers, but were able to successfully cure their condition using Eucalyptus tea. Thus, Eucalyptus became well known throughout Europe and the Mediterranean as the Australian fever tree.

The essential oil in the leaves is commonly used for medicinal purposes. The essential oil from the fruit, buds, and branches contain from 15-60% of 1,8-cineole (eucalyptol). Activities attributed to this compound include: anaesthetic, antiseptic, expectorant, antitussive, counterirritant and sedative. Eucalyptus oil is said to function in a fashion similar to that of menthol by acting on receptors in the nasal mucosa, leading to a reduction in symptoms such as nasal congestion.

Camphor is a pungent white crystalline substance obtained from the *Cimmamonurn camphora* tree or made synthetically.

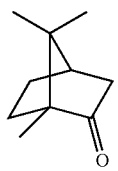

It is used in medicine as a stimulant, diaphoretic and inhalant. Camphor has been found beneficial in asthma and spasmodic cough and the powder may be used as a snuff for the relief of nervous headache and catarrh. It has found use as a 1% solution against catarrhal disease, both acute and chronic. Good results have likewise being reported from its use in sore throat and acute bronchitis.

Menthol is a compound obtained from peppermint oil or other mint oils or made synthetically. Menthol has local anaesthetic and counterirritant qualities, and has the following chemical structure:

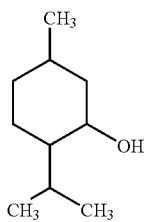

Menthol induces cold sensations when applied to the skin and mucosal membranes, the underlying mechanism being a stimulating action on peripheral cold receptors. This stimulation of cold receptors is independent of any change in temperature. Cold receptor activity is proposed to be controlled by a calcium stimulated outward current. It is hypothesized that menthol induces a calcium inactivation, preventing the efflux of calcium from intracellular space, which loosen the control of this mechanism and increases the afferent activity of cold sensors. Calcium application completely abolishes the stimulating menthol effect on cold receptors. The coolant action of menthol has been extensively discussed by Eccles in 1994 who showed that the activation of cold receptors by calcium channel blocking activity resulted in cold sensation within the nose which produced the sensation of a free decongested nose. Therefore menthol probably selectively stimulates cold receptors by impeding calcium current.

*Pinus sylvestris/Pumilius*: Pine oil is extracted from the needles (pine needle oil) as well as twigs and buds (pine oil) of pine trees by steam distillation in yields of 0.1-0.5%. Constituents of pine oil include 50-97% monoterpene hydrocarbons, such as α-pinene, with lesser amounts of 3-carene, dipentene, β-pinen, D-limonene, α-terpinene, γ-terpinene, cis-β-ocimene, myrcene, camphene, sabinene, and terpinolene. The approved modern therapeutic applications for pine needle oil are based on its history of use in well established systems of traditional and conventional medicines, and on phytochemical investigations and pharmacological studies.

In Germany, pine needle oil is official in the German Pharmacopoeia, the Standard Licenses for Finished Drugs Monographs, and it is also approved by Commission E. Drops of the essential oil are added to boiling water for inhalation of steam vapor as a supportive treatment for catarrhal diseases of the respiratory tract. The drops are also applied topically by carefully rubbing into the skin for rheumatic complaints. In German pediatric medicine, Pumilio pine oil is used as a component of "Inhalatio composite" formulation (eucalyptus oil 45%, Pumilio pine oil 45%, peppermint oil 10%), intended especially for coryza (acute cold and nasal inflammation) and nasal catarrh in children. The Commission E reports secretolytic, hyperemic, and slight antiseptic activity.

Pine Oil: In the United States, pine needle oil, distilled from the leaves of dwarf pine, is official in the National Formulary. It is used as a component in cough and cold medicines, vaporizer fluids, nasal decongestants, and analgesic ointments. The essential oil of Scots pine (*P. sylvestris*) is also used in aromatherapy. Pumilius Essential Oil (extracted by Mountain Pine) contains a mix of triterpens hydrocarbouns like Alfa and Beta pinene, limonene, fellandrene, canfene and borneol, which have antiseptic and decongestant action. Given the volatility of these compounds, they have a high therapeutic action especially on breathing mechanisms.

Bitter orange (*Citrus aurantium*) oil is extracted from the bitter orange flower and peel and used to treat sore throat. This essential oil has a euphoric, invigorating, cooling and balancing effect on the mind. On the physical side, it is an antispasmodic, antiseptic, disinfectant and anti fever agent. In the natural tradition it is use as a remedy for cough and cold.

Lavender: The volatile essential oil of lavender contains many constituents, including perillyl alcohol and linalool. The oil is thought to be calming and thus can be helpful in some cases of insomnia. One trial of elderly people with sleeping troubles found that inhaling lavender oil was as effective as some commonly prescribed sleep medications. A large clinical trial found that lavender oil added to a bath was no more effective than a placebo for relieving perineal discomfort immediately after childbirth. However, perineal pain was reduced three to five days afterward.

Lavender is recommended by the German Commission E monograph for indigestion and nervous intestinal discomfort. The German Commission E monograph suggests 1-2 teaspoons (5-10 grams) of the herb be taken as a tea. For internal applications, ½-¾ teaspoon (2-4 ml) of tincture can be taken two or three times per day. Several drops of the oil can be added to a bath or diluted in vegetable oil for topical applications. The concentrated oil is not for internal use, except under medical supervision.

SUMMARY OF THE INVENTION

Through intensive study and investigation, the inventors have discovered new cream formulations of essential oils, especially adapted for use in a stick-type dispensing apparatus, that do not contain a preservative, but that remain free from bacterial contamination during the life of the product. Accordingly, in a first embodiment the invention provides a preservative-free non-petrolatum decongestant cream composition comprising (a) from 70 to 90 weight parts of water; (b) from 0.5 to 10 weight parts of one or more active ingredients selected from menthol, camphor, eucalyptus oil, pine oil, orange oil and lavender; (c) from 6 to 10 weight parts of propylene glycol, butylene glycol or pentylene glycol; (d) from 0.5 to 2.0 weight parts cetearyl alcohol; (e) from 0.5 to 2.0 weight parts carbomer; and (f) from 4 to 6 weight parts of (i) 1,2-hexanediol and caprylyl glycol (component (i)) and (ii) 2-methyl-1,3-propanediol (component (ii)), at a ratio of component (i) to component (ii) of from about 1:1 to about 1:5.

In another embodiment the invention provides a device for administering vapour or aromatic therapy comprising said composition dispensed by an applicator that comprises (a) a rigid shell having a hollow interior, an open top, a closed bottom, and a uniform cross section from the bottom to the top; and (b) means for urging the contents of said shell out of said open top.

In still another embodiment the invention provides a method of making a preservative-free non-petrolatum decongestant cream composition comprising (a) mixing in a first tank from 70 to 90 weight parts water and from 0.5 to 2.0 weight parts of carbomers to form a gel; (b) heating said gel to 60-65° C.; (c) mixing from 0.5 to 2.0 weight parts of melted cetearyl alcohol at about 65-70° C. with said gel, to form an emulsion; (d) cooling said emulsion to room temperature; (e) dissolving in a separate tank from 0.5 to 10 weight parts of one or more active ingredients selected from menthol, camphor, eucalyptus oil, pine oil, orange oil and lavender in from 4 to 6 weight parts of (i) 1,2-hexanediol and caprylyl glycol (component (i)) and (ii) 2-methyl-1,3-propanediol (component (ii)), at a ratio of component (i) to component (ii) of from about 1:1 to about 1:5, to form an essential oil mixture; (f) dispersing said essential oil mixture in said emulsion to form a cream; and (g) neutralizing said cream with from 0.2 to 0.5 weight parts sodium hydroxide.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

The accompanying drawings, which are incorporated in and constitute a part of this specification, illustrate several embodiments of the invention and together with the description, serve to explain the principles of the invention.

DESCRIPTION THE INVENTION

Figure 1:
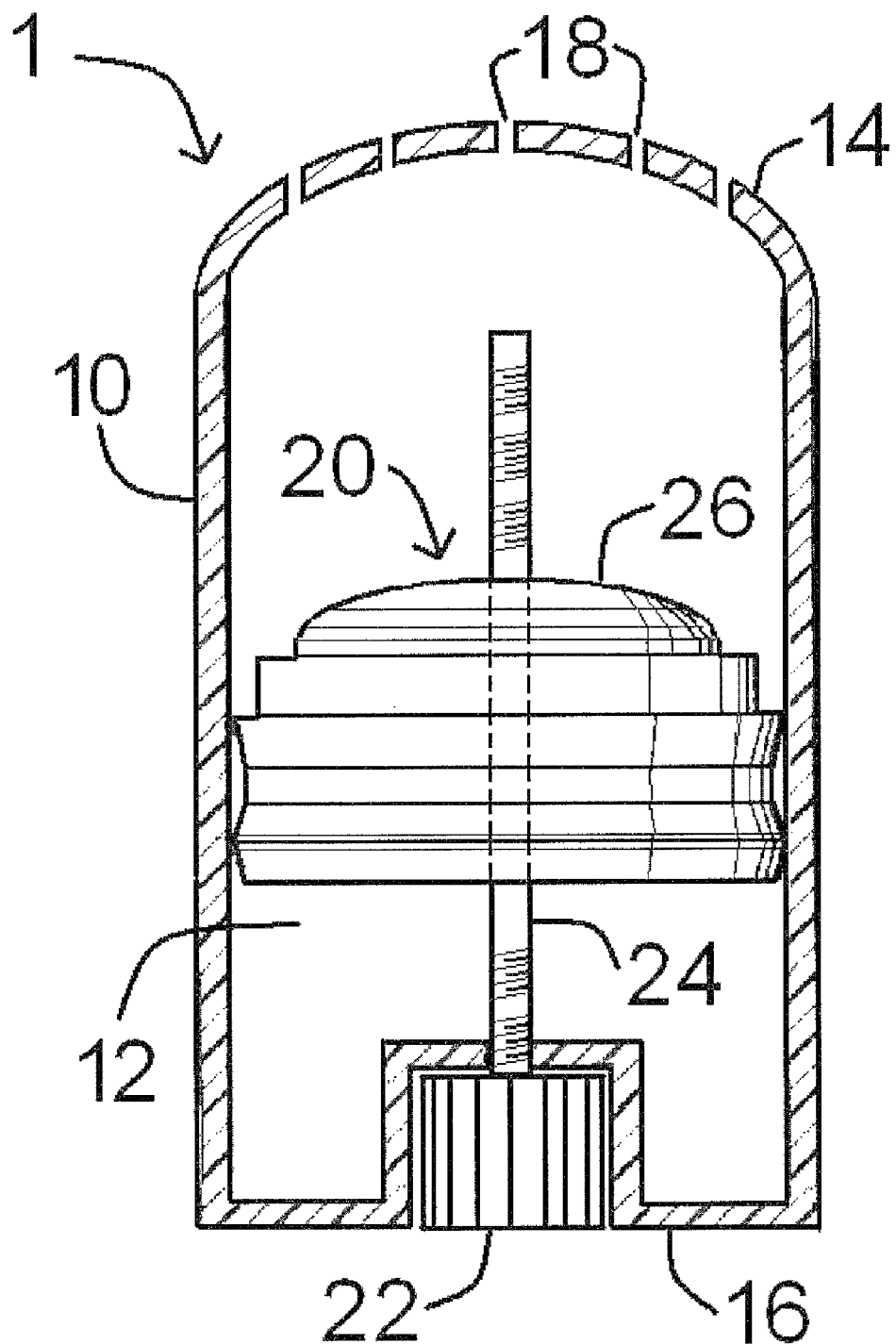
FIG. 1 is an illustrative structure for the dispensing device of the present invention.

The present invention may be understood more readily by reference to the following detailed description of preferred embodiments of the invention and the Examples included therein.

Definitions and Use of Terms

As used in this specification and in the claims, which follow, the singular forms "a," "an" and "the" include plural referents unless the context clearly dictates otherwise. Thus, for example, reference to "an ingredient" includes mixtures of ingredients; reference to "an active pharmaceutical agent" includes more than one active pharmaceutical agent, and the like.

"Pharmaceutically acceptable" means that which is useful in preparing a pharmaceutical composition that is generally safe, non-toxic and neither biologically nor otherwise undesirable and includes that which is acceptable for human pharmaceutical use. Each of the ingredients described in this document is pharmaceutically acceptable.

"Therapeutically effective amount" means that amount which, when administered to an animal for treating or preventing a disease, is sufficient to effect such treatment or prevention for the disease, or to provide relief from the disease. The active ingredients described in this document are always present in a therapeutically effective amount.

When ranges are given by specifying the lower end of a range separately from the upper end of the range, it will be understood that the range can be defined by selectively combining any one of the lower end variables with any one of the upper end variables that is mathematically possible.

When used herein the term "about" or "ca." will compensate for variability allowed for in the pharmaceutical industry and inherent in pharmaceutical products, such as differences in product strength due to manufacturing variation and time-induced product degradation.

"Preservative" may be defined by reference to Annex VI of the current version of European Directive on cosmetic products (76/768), which defines a preservative as any of the following ingredients, or their salts or esters: benzoic acid; propionic acid; salicylic acid; sorbic acid; formaldehyde; paraformaldehyde; biphenyl-2-ol; pyrithione zinc; inorganic sulphites and hydrogensulphites; sodium iodate; chlorobutanol; 4-hydroxybenzoic acid; 3-acetyl-6-methylpyran-2,4 (3H)-dione; formic acid; 3,3'-dibromo-4,4'-hexamethylenedioxydibenzamidine; thiomersal; phenylmercuric salts; undec-10-enoic acid and salts; hexetidine; 5-bromo-5-nitro-1,3 dioxane; bronopol; 2,4-dichlorobenzyl alcohol; triclocarban; 4-chloro-m-cresol; triclosan; 4-chloro-3,5-xylenol; 3,3'-bis(1-hydroxymethyl-2,5-dioxoimidazolidin-4-y1)-1,1'-methylenediurea; poly(1-hexamethylenebiguanide) hydrochloride; 2-phenoxyethanol; hexamethylenetetramine; methenamine 3-chloroallylochloride; 1-(4-chlorophenoxyl)-1-(imidazol-1-y1)-3,3-dimethylbutan-2-one; 1,3-bis(hydroxymethyl)-5,5-dimethylimidazolidine-2,4-dione; benzyl alcohol; 1-hydroxy-4-methyl-6(2,4,4-trimethylpentyl)-2-pyridon; 1,2-dibromo-2,4-dicyanobutane; 6,6-dibromo-4,4-dichloro-2,2'-methylenediphenol (bromochlorophen); 4-isopropyl-m-cresol; mixture of 5-chloro-2-methyl-isothiazol-3 (2H)-one with magnesium chloride and magnesium nitrate; 2-benzyl-4-chlorophenol (chlorophene); 2-chloroacetamide; chlorhexidine (INN) and its digluconate, diacetate and dihydrochloride; 1-phenoxypropan-2-ol; alkyl (C12-C22) trimethyl ammonium, bromide and chloride; 4,4-dimethyl-1,3-oxazolidine; N-(hydroxymethyl)-N-(dihydroxymethyl-1,3-dioxo-2,5-imidazolinidyl-4)-N'-(hydroxymethyl)urea; 1,6-Di(4-amidinophenoxy)-n-hexane; glutaraldehyde; 5-ethyl-3, 7-dioxa-1-azabicyclo octane; 3-(p-chlorophenoxy)-propane-1,2-diol; sodium hydroxymethylamino acetate; silver chloride deposited on titanium dioxide; benzethonium chloride; benzalkonium chloride, bromide and saccharinate; benzylhemiformal; 3-iodo-2-propynyl butylcarbamate.

Alternatively, a preservative can be defined by its biocidal properties, as defined by its ability to inhibit bacterial growth (minimum inhibitory concentration or MIC) or to kill bacteria (minimum lethal concentration or MLT). In one embodiment, the preservative has a MIC of less than 1, 2, 5, or 10% against one or more bacterial and fungal species selected from *staphylococcus aureus, streptococcus agalactiae, streptococcus faecalis, eschericia coli, proteus vulagris, mycobacterium smegmatis, klebsiella pneumonia, pseudomonas aeruginosa, pseudomonas cepacia, pseudomonas fluorescens, pseudomonas oleovorans, corynebacterium xerosis, micrococcus luteus, bacillus cereus, ravobacter suaveolens, enterobacter aerogenes, serratia marcescens, shigella sonnei, salmonella typhosa, aspergillus niger, candida albicans, candida parapsilosis, chaetomium globosum, cladosporium resinae, gliocladium fimbriatum,* and *penicillium notatum.* In another embodiment, the preservative has a MLC of less than 1, 2, 5 or 100% against one or more of the foregoing bacterial and fungal species.

Discussion

As discussed above, the invention provides a preservative-free non-petrolatum decongestant cream composition comprising (a) from 70 to 90 weight parts of water; (b) from 0.5 to 10 weight parts of one or more active ingredients selected from menthol, camphor, eucalyptus oil, pine oil, orange oil and lavender; (c) from 6 to 10 weight parts of propylene glycol, butylene glycol or pentylene glycol; (d) from 0.5 to 2.0 weight parts cetearyl alcohol (preferably 1.0 weight parts); (e) from 0.5 to 2.0 weight parts carbomer; and (f) from 4 to 6 weight parts (preferably 5 weight parts) of (i) 1,2-hexanediol and caprylyl glycol (component (i)) and (ii) 2-methyl-1,3-propanediol (component (ii)), at a ratio of component (i) to component (ii) of from about 1:1 to about 1:5 (preferably 1:3).

The active ingredients are preferably present in a pharmaceutically effective amount, and in one embodiment the cream comprises about 1.0 weight parts of eucalyptus essential oil, about 0.2 weight parts *Pinus sylvestris* essential oil, and about 0.02 weight parts lavender essential oil. In another embodiment, the cream comprises about 4.6 weight parts camphor, about 2.0 weight parts menthol, and about 1.0 weight parts eucalyptus oil. In still another embodiment the composition comprises about 0.8 weight parts *Pinus pumilius* essential oil. In yet another embodiment the composition comprises about 4.8 weight parts camphor, about 2.6 weight parts menthol, and about 1.2 weight parts eucalyptus essential oil.

While various alkane diols can be used in the formulations of the present invention, propylene glycol, butylene glycol and pentylene glycol are preferred, with propylene glycol most preferred. The propylene glycol is preferably present at 6 to 10 weight parts, preferably about 7 to 9 weight parts, and most preferably about 8 weight parts.

The carbomer component preferably comprises carbomer 980 in addition to carbomer 1382. The composition preferably comprises from about 0.5 to 1.0 weight parts carbomer 980, most preferably about 0.65 weight parts carbomer 980. The composition preferably comprises from 0.25 to 0.5 weight parts carbomer 1382.

The cream is preferably present in the form of a stick, and can also be defined by its viscosity. In various embodiments, the cream has a viscosity at 25° C. (Viscosimeter Brookfield DV II+Pro spindle 6 2.5 rpm) of greater than 100,000, 200,000, 300,000, or even 400,000 mPas, and less than 600,000 or 500,000 mPas.

The cream can also be defined by its pH, and in various embodiments the pH of the cream ranges from 4-9, or 5-8. The pH of the cream is preferably from 5.5 to 7.0

In still another embodiment the invention provides a method of making a preservative-free non-petrolatum decongestant cream composition comprising (a) mixing in a first tank from 70 to 90 weight parts water and from 0.5 to 2.0 weight parts of carbomers to form a gel; (b) heating said gel to 60-65° C.; (c) mixing from 0.5 to 2.0 weight parts of melted cetearyl alcohol (preferably about 1.0 weight parts) at about 65-70° C. with said gel, to form an emulsion; (d) cooling said emulsion to room temperature; (e) dissolving in a separate tank from 0.5 to 10 weight parts of one or more active ingredients selected from menthol, camphor, eucalyptus oil, pine oil, orange oil and lavender in from 4 to 6 weight parts of (i) 1,2-hexanediol and caprylyl glycol (component (i)) and (ii) 2-methyl-1,3-propanediol (component (ii)), at a ratio of component (i) to component (ii) of from about 1:1 to about 1:5, to form an essential oil mixture; (f) dispersing said essential oil mixture in said emulsion to form a cream; and (g) neutralizing said cream with from 0.2 to 0.5 weight parts sodium hydroxide.

Propylene glycol (or another alkane diol) is also important to the composition, and in one embodiment from 6 to 10, from 7 to 9, or about 8 weight parts of propylene glycol, butylene glycol or pentylene glycol is mixed in said first tank in step (a). In an alternative embodiment, from 6 to 10, from 7 to 9, or about 8 weight parts of propylene glycol, butylene glycol or pentylene glycol is mixed in said separate tank in step (e). In still another embodiment from 0.5 to 2.0 weight parts of melted cetearyl alcohol, and about 0.05 weight parts tocopheryl acetate at about 65-70° C. are mixed with said gel in step (c).

The cream is filled in a device that allows one to apply the cream directly without touching the cream with the hands. Once applied, the composition emits vapors that can be inhaled by the patient. Therefore, in another embodiment the invention provides a device for administering vapour or aromatic therapy comprising said composition dispensed by an applicator that comprises (a) a rigid shell having a hollow interior, an open top, a closed bottom, and a uniform cross section from the bottom to the top; and (b) means for urging the contents of said shell out of said open top.

Referring now to the drawings, FIG. 1 illustrates an exemplary embodiment of an applicator 1. The applicator 1 comprises a rigid shell 10 having a hollow interior 12, an open top 14, and a closed bottom 16. In a particular embodiment, the open top 14 includes one or more holes 18.

The applicator 1 includes a means 20 for urging the contents of the shell 10 out of said open top 14. In a particular embodiment, the means 20 comprises a rotatable wheel 22, a spindle 24, and an elevator 26. The rotatable wheel 22 can be rotated in order to turn the spindle 24. The turning of the spindle 24 causes the elevator 26 to rise vertically, which in turn causes the elevator 26 to urge the contents of the shell 10 out of said open top 14.

In a particular embodiment, the rotatable wheel 22 is exposed and can be turned by a user's hand. In another embodiment, the rotatable wheel 22 is in connection with an actuating device (not shown) such as a button, and the wheel 22 and can be turned by a user's hand pressing the actuating device. Suitable actuating devices for turning the wheel 22 are described, for example, in U.S. Pat. Nos. 5,839,622 and 6,592,278.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to

Example 1

Balsamic Cream for Adults

| Ingredients | |
| --- | --- |
| Water | to 100% |
| Propylene Glycol | 8.00% |
| Camphor | 4.60% |
| Methylpropanediol | 3.75% |
| Menthol | 2.00% |
| Hexanediol and Caprylyl glycol | 1.25% |
| *Eucalyptus* essential oil | 1.00% |
| Cetearyl alcohol | 1.00% |
| Carbomer 980 | 0.65% |
| Carbomer 1382 | 0.33% |
| Sodium Hydroxide (30% solution) | 1.00% |

Production Method

In the main tank of the production equipment add water, heating until +40° C. Sprinkle the carbomers in the aqueous solution using a homogenizer for suitable gel formation. Heat the aqueous phase at 60-65° C.

In a side kettle heat at 65-70° C. until Cetearyl Alcohol is melted, then transfer into main tank homogenising to emulsify. Cool down the temperature to room temperature.

In an appropriate container dissolve camphor, menthol and eucalyptus essential oil in Propylene glycol, Methylpropanediol and Hexanediol, Caprylyl glycol, add to the mass homogenising to obtain a complete dispersion. Neutralise the mass with NaOH (30% solution in water).

Challenge Test Method (Used for all the Challenge Tests Reported in this Document):

The Challenge test is a predictive method useful to evaluate the effectiveness of a preservative system in cosmetics products and hence to check their stability. Performing an artificial contamination of cosmetics products by means of different ATTC micro-organisms we can simulate the situation which can be found in the production, storage and use life of the product itself.

The production process for cosmetics does not require sterility and for this reason there is always a default level of environmental microbiological contamination that must be kept under control by a proper preservative system. In addition, the normal use of the product by the consumer causes further repeated contamination.

In the Challenge test, we oversize the experimental conditions by inoculating a large amount of micro-organisms that hardly can be found in normal environmental conditions. In this case, the inoculum has been represented by four different ATTC microbial strains and we have evaluated microbial growth decay at four different time points (48 h, 7 d, 14 d and 28 d).

| STRAINS UTILIZED |
| --- |
| *Staphylococcus aureus* ATCC 6538 |
| *Pseudomonas aeruginosa* ATCC 9027 |
| *Candida albicans* ATCC 10231 |
| *Aspergillus niger* ATCC 16404 |

Challenge Test Results

| Time | Count | Log(10) | Log reduction | Min Value Ref. E.Ph. |
| --- | --- | --- | --- | --- |
| *Staphylococcus aureus* | | | | |
| T0 | 2.75E+05 | 5.44 | | |
| 2 day | 1.00E+00 | 0.00 | 5.44 | 2 |
| 7 day | 1.00E+00 | 0.00 | 5.44 | 3 |
| 14 day | 1.00E+00 | 0.00 | 5.44 | == |
| 28 day | 1.00E+00 | 0.00 | 5.44 | No increase |
| *Pseudomonas aeruginosa* | | | | |
| T0 | 2.00E+06 | 6.30 | | |
| 2 day | 1.00E+00 | 0.00 | 6.30 | 2 |
| 7 day | 1.00E+00 | 0.00 | 6.30 | 3 |
| 14 day | 1.00E+00 | 0.00 | 6.30 | == |
| 28 day | 1.00E+00 | 0.00 | 6.30 | No increase |
| *Candida albicans* | | | | |
| T0 | 1.44E+06 | 6.16 | | |
| 2 day | 1.00E+00 | 0.00 | 6.16 | == |
| 7 day | 1.00E+00 | 0.00 | 6.16 | == |
| 14 day | 1.00E+00 | 0.00 | 6.16 | 2 |
| 28 day | 1.00E+00 | 0.00 | 6.16 | No increase |
| *Aspergillus niger* | | | | |
| T0 | 3.10E+05 | 5.49 | | |
| 2 day | 1.00E+00 | 0.00 | 5.49 | == |
| 7 day | 1.00E+00 | 0.00 | 5.49 | == |
| 14 day | 1.00E+00 | 0.00 | 5.49 | 2 |
| 28 day | 1.00E+00 | 0.00 | 5.49 | No increase |

Conclusion:

The data obtained by the test demonstrate that the composition meets criterion recommended by the European Pharmacopeia current edition for bacterial control in a topical product.

Example 2

Balsamic Cream for Children

| Ingredients | |
| --- | --- |
| Water | to 100% |
| Propylene Glycol | 8.00% |
| Methylpropanediol | 3.75% |
| Hexanediol and Caprylyl glycol | 1.25% |
| *Eucalyptus* essential oil | 1.00% |
| Cetearyl alcohol | 1.00% |
| Carbomer 980 | 0.65% |
| Carbomer 1382 | 0.33% |
| Sodium Hydroxide (30% solution) | 1.00% |
| *Pinus Sylvestris* essential oil | 0.20% |
| Lavender essential oil | 0.02% |

Production Method

In the main tank, add water and propylene glycol and heat to 40° C. Sprinkle the carbomers into the aqueous solution using a homogenizer suitable for gel formation. Heat the aqueous phase at 60-65° C.

In a side kettle, heat cetearyl alcohol to 65-70° C. until it is melted, and then transfer the alcohol to the main tank and homogenize/emulsify. Cool the resultant mass to room temperature.

In a separate container mix the essential oils with methylpropanediol and hexanediol, and caprylyl glycol, and add to the mass the main tank while homogenizing to obtain a complete dispersion. Neutralise the resultant mass with NaOH (300% solution in water).

Challenge Test Results:

| Time | Count | Log(10) | Log reduction | Min Value Ref. E.Ph. |
|---|---|---|---|---|
| *Staphylococcus aureus* | | | | |
| T0 | 3.60E+05 | 5.56 | | |
| 2 day | 1.00E+00 | 0.00 | 5.56 | 2 |
| 7 day | 1.00E+00 | 0.00 | 5.56 | 3 |
| 14 day | 1.00E+00 | 0.00 | 5.56 | == |
| 28 day | 1.00E+00 | 0.00 | 5.56 | No increase |
| *Pseudomonas aeruginosa* | | | | |
| T0 | 1.80E+06 | 6.25 | | |
| 2 day | 1.00E+00 | 0.00 | 6.25 | 2 |
| 7 day | 1.00E+00 | 0.00 | 6.25 | 3 |
| 14 day | 1.00E+00 | 0.00 | 6.25 | == |
| 28 day | 1.00E+00 | 0.00 | 6.25 | No increase |
| *Candida albicans* | | | | |
| T0 | 2.40E+05 | 5.38 | | |
| 2 day | 1.00E+00 | 0.00 | 5.38 | == |
| 7 day | 1.00E+00 | 0.00 | 5.38 | == |
| 14 day | 1.00E+00 | 0.00 | 5.38 | 2 |
| 28 day | 1.00E+00 | 0.00 | 5.38 | No increase |
| *Aspergillus niger* | | | | |
| T0 | 1.00E+06 | 6.00 | | |
| 2 day | 1.00E+00 | 0.00 | 6.00 | == |
| 7 day | 1.00E+00 | 0.00 | 6.00 | == |
| 14 day | 1.00E+00 | 0.00 | 6.00 | 2 |
| 28 day | 1.00E+00 | 0.00 | 6.00 | No increase |

Conclusion

The data obtained by the test demonstrate that the composition meets criterion recommended by the European Pharmacopeia current edition for bacterial control in a topical product.

Example 3

Balsamic Cream for Children

| Ingredients | |
|---|---|
| Water | to 100% |
| Propylene Glycol | 8.00% |
| Methylpropanediol | 3.75% |
| Hexanediol and Caprylyl glycol | 1.25% |
| Cetearyl alcohol | 1.00% |
| Carbomer 980 | 0.65% |
| Carbomer 1382 | 0.33% |
| Sodium Hydroxide (30% solution) | 1.00% |
| *Pinus Pumilius* essential oil | 0.80% |
| Tocopheryl Acetate | 0.05% |

Production Method

In the main tank, mix water and propylene glycol and heat to 40° C. Sprinkle the carbomers in the aqueous solution using a homogenizer suitable for gel formation. Heat the aqueous phase at 60-65° C.

In a side kettle heat the cetearyl alcohol to 65-70° C. so that it melts, then add tocopheryl acetate and mix until homogenous. Transfer the mass into the main tanks and homogenize/emulsify. Cool to room temperature.

In a separate container, mix the *Pinus pumilius* essential oil with methylpropanediol and hexanediol, and caprylyl glycol. Add the mass to the main tank and homogenize to obtain a complete dispersion. Neutralise the resulting mass with NaOH (30% solution in water).

Challenge Test Results

| Time | Count | Log(10) | Log reduction | Min Value Ref. E.Ph. |
|---|---|---|---|---|
| *Staphylococcus aureus* | | | | |
| T0 | 3.00E+05 | 5.48 | | |
| 2 day | 1.00E+00 | 0.00 | 5.48 | 2 |
| 7 day | 1.00E+00 | 0.00 | 5.48 | 3 |
| 14 day | 1.00E+00 | 0.00 | 5.48 | == |
| 28 day | 1.00E+00 | 0.00 | 5.48 | No increase |
| *Pseudomonas aeruginosa* | | | | |
| T0 | 2.20E+06 | 6.34 | | |
| 2 day | 1.00E+00 | 0.00 | 6.34 | 2 |
| 7 day | 1.00E+00 | 0.00 | 6.34 | 3 |
| 14 day | 1.00E+00 | 0.00 | 6.34 | 6.25 |
| 28 day | 1.00E+00 | 0.00 | 6.34 | No increase |
| *Candida albicans* | | | | |
| T0 | 2.00E+06 | 6.30 | | |
| 2 day | 1.00E+00 | 0.00 | 6.30 | == |
| 7 day | 1.00E+00 | 0.00 | 6.30 | == |
| 14 day | 1.00E+00 | 0.00 | 6.30 | 2 |
| 28 day | 1.00E+00 | 0.00 | 6.30 | No increase |
| *Aspergillus niger* | | | | |
| T0 | 1.10E+06 | 6.04 | | |
| 2 day | 1.00E+00 | 0.00 | 6.04 | == |
| 7 day | 1.00E+00 | 0.00 | 6.04 | == |
| 14 day | 1.00E+00 | 0.00 | 6.04 | 2 |
| 28 day | 1.00E+00 | 0.00 | 6.04 | No increase |

Conclusion

The data obtained by the test demonstrate that the composition meets criterion recommended by the European Pharmacopeia current edition for bacterial control in a topical product.

Peroxide Stability of Example 3 Formulation

To guarantee the safety in children, it is very important to minimize the peroxide content of a cream. To ensure adequate safety, the peroxide content of the formulation reported in the example 3 was checked at +25° C. and +40° C., as reported in the following tables. After 6 month stability testing at +40° C., the quantity of peroxide is lower than 10 micromole/liter.

| | 25° C. (RH = 60%) | |
|---|---|---|
| Time (months) | Appearance of Balsamic Cream | Average Ip <10 milliequivalent of active oxygen/1000 g |
| Specifications | | |
| 0 | White and Viscous cream | 0.853 |
| 1 | White and Viscous cream | 0.544 |
| 3 | White and Viscous cream | 1.295 |
| 6 | White and Viscous cream | 1.572 |

| Time (months) | Appearance of Balsamic Cream | Average Ip <10 milliequivalent of active oxygen/1000 g |
|---|---|---|
| | Specifications | |
| 0 | White and Viscous cream | 0.853 |
| 1 | White and Viscous cream | 0.708 |
| 3 | White and Viscous cream | 2.993 |
| 6 | White and Viscous cream | 3.364 |

40° C. (RH = 75%)

Example 4

Balsamic Cream for Adults

| Ingredients | |
|---|---|
| Water | to 100% |
| Propylene Glycol | 8.00% |
| Camphor | 4.80% |
| Methylpropanediol | 3.75% |
| Menthol | 2.60% |
| Hexanediol and Caprylyl glycol | 1.25% |
| *Eucalyptus* essential oil | 1.20% |
| Cetearyl alcohol | 1.00% |
| Carbomer 980 | 0.65% |
| Carbomer 1382 | 0.33% |
| Sodium Hydroxide (30% solution) | 1.00% |

Production Method

In the main tank of the production equipment add water, heating until +40° C. Sprinkle the carbomers into the aqueous solution using a homogenizer suitable for the gel formation. Heat the aqueous phase to 60-65°.

In a side kettle, heat the cetearyl alcohol to 65-70° C. so that the alcohol melts, and then transfer to the main tank for homogenization/emulsification. Cool the mass to room temperature.

In a separate container dissolve camphor, menthol and eucalyptus essential oil in propylene glycol, methylpropanediol and hexanediol, and caprylyl glycol. Add the mass to the main tank and homogenize to obtain a complete dispersion. Neutralise the mass with NaOH (30% solution in water).

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A kit for administering aromatic therapy comprising:
    a) an applicator comprising:
        a rigid shell having a hollow interior, an open top, a closed bottom, and a uniform cross section from the bottom to the top; and
    b) a preservative-free non-petrolatum decongestant cream composition in said shell comprising:
        i) from 70 to 90 weight parts of water;
        ii) from 0.5 to 10 weight parts of one or more active ingredients selected from menthol, camphor, eucalyptus oil, pine oil, orange oil and lavender;
        iii) from 6 to 10 weight parts of propylene glycol, butylene glycol or pentylene glycol;
        iv) from 0.5 to 2.0 weight parts cetearyl alcohol;
        v) from 0.5 to 2.0 weight parts carbomer; and
        vi) from 4 to 6 weight parts of (a) 1,2-hexanediol and caprylyl glycol (component (a)) and (b) 2-methyl-1, 3-propanediol (component (b)), at a weight ratio of component (a) to component (b) of from about 1:1 to about 1:5.

2. The kit of claim 1, part (vi) wherein said composition comprises a weight ratio of component (a) to component (b) of about 1:3.

3. The kit of claim 1 wherein said composition comprises from 0.5 to 2.0 weight parts of carbomers 980 and 1382.

4. The kit of claim 1 wherein said composition has a pH of 5.5-7.00.

5. The kit of claim 1 wherein said composition has a viscosity of from 200.000 to 600.000 mPas at 25° C.

6. The kit of claim 1 wherein said open top comprises a cap comprising one or more openings.

7. The kit of claim 1 further comprising a means for urging the contents of said shell out of said open top, wherein said means for urging the contents of said shell out of said open top comprises a rotatable wheel, a spindle, and an elevator, physically integrated as one unit such that rotation of the rotatable wheel turns the spindle and causes the elevator to rise vertically.

* * * * *